(12) United States Patent
Marshall et al.

(10) Patent No.: US 7,736,343 B2
(45) Date of Patent: Jun. 15, 2010

(54) MEDICAL INJECTION DEVICES

(75) Inventors: Jeremy Marshall, Oxford (GB); Rury Reginald Holman, Oxford (GB)

(73) Assignee: Owen Mumford Limited, Oxford (GB)

( * ) Notice: Subject to any disclaimer, the term of this patent is extended or adjusted under 35 U.S.C. 154(b) by 1203 days.

(21) Appl. No.: 10/500,567

(22) PCT Filed: Jan. 10, 2003

(86) PCT No.: PCT/GB03/00071

§ 371 (c)(1),
(2), (4) Date: Jun. 30, 2004

(87) PCT Pub. No.: WO03/057285

PCT Pub. Date: Jul. 17, 2003

(65) Prior Publication Data

US 2005/0090782 A1 Apr. 28, 2005

(30) Foreign Application Priority Data

Jan. 10, 2002 (GB) .................................. 0200444.8

(51) Int. Cl.
*A61M 5/00* (2006.01)
(52) U.S. Cl. ....................... 604/207; 604/211
(58) Field of Classification Search ................. 604/187, 604/207, 208, 209, 211, 246, 134, 135, 136
See application file for complete search history.

(56) References Cited

U.S. PATENT DOCUMENTS

| 5,279,585 | A | * | 1/1994 | Balkwill | ...................... 604/207 |
| 5,645,534 | A | | 7/1997 | Chanoch | |
| 5,674,204 | A | * | 10/1997 | Chanoch | ...................... 604/211 |
| 6,059,755 | A | | 5/2000 | Michel | |
| 6,086,567 | A | * | 7/2000 | Kirchhofer et al. | ........... 604/211 |

FOREIGN PATENT DOCUMENTS

| EP | 0 554 996 | 8/1993 |
| EP | 0 688 572 | 9/2000 |
| WO | WO 96/07443 | 3/1996 |
| WO | 96/26754 | 9/1996 |

* cited by examiner

*Primary Examiner*—Nicholas D Lucchesi
*Assistant Examiner*—Christopher D Koharski
(74) *Attorney, Agent, or Firm*—Young & Thompson

(57) ABSTRACT

A knob is rotated from its zero position to set a dose. This rotates an indexer, which through its peg turns a ring by pushing on one of the teeth. A position is reached wherein the free end portion of the peg meets a cam surface. On continued rotation of the knob, the peg is forced radially inwards to clear the tooth that it has just been pushing against. The ring, having been shifted through one-seventh of a complete revolution is then left stationary while the knob is turned further to whatever dose is required. When a syringe actuation trigger is pressed, the knob winds back again to its zero position, taking with it the indexer. The peg is still held clear of the ring until it hits the sloping side of the tooth following the one which it had previously pushed.

20 Claims, 7 Drawing Sheets

MEDICAL INJECTION DEVICES

Figure 1:
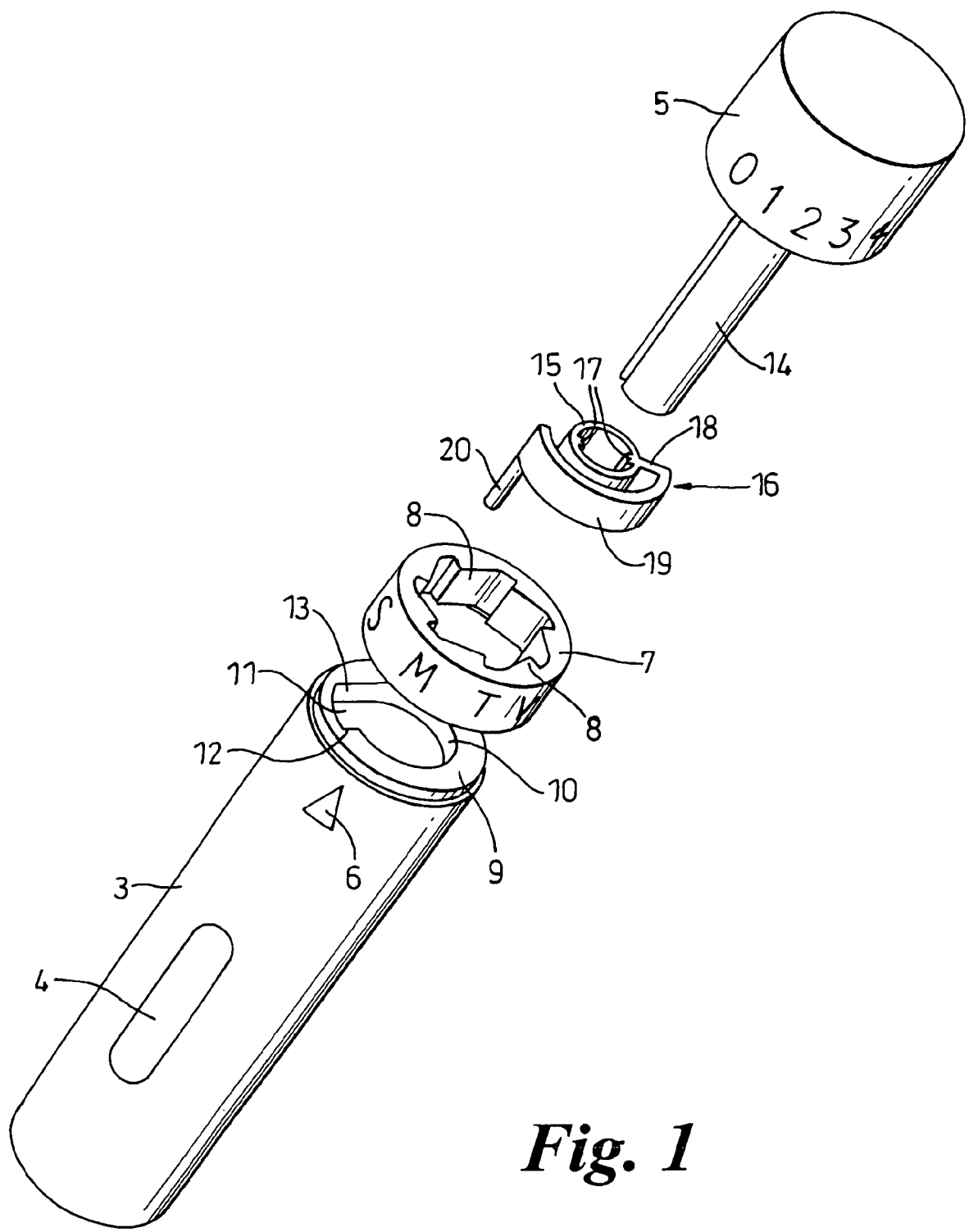

This invention relates to medical injection devices. It is of course of great importance that when an injection is carried out the correct dosage is delivered. Many injection devices can administer fixed doses or have some arrangement for setting them up so that, when actuated, the desired correct dose is automatically ejected from the needle. A common design is to have a knob at the rear end of the device which is turned against a scale to indicate the dose, this at the same time adjusting the travel of the syringe plunger when the device is actuated.

However, there is also the matter of delivering the correct number of injections per day, per week or per month. It is quite easy, particularly for people with non-routine lives, to miss an injection, or even to administer an extra one having forgotten that an appropriate injection has already been given. It is not known that any current injection devices provide guidance to help the user maintain regular use.

According to one aspect of the present invention there is provided a dose application counter for an injection device with a dose setting element, the counter having a member with a lost motion connection to the dose setting element, whereby movement of said element by and beyond a predetermined amount causes movement of said member to a set extent, each such movement of said member resulting in the indication of usage of the injection device.

One preferred embodiment of the present invention is in the form having a dose setting knob rotatable with respect to the body of the device, the counter comprising a rotatable ring with an annular array of projections co-axial with the knob, the minimum dose requiring the knob to be turned from a zero position through an angle at least as great as the angular spacing of adjacent projections, an element rotatable with the knob and spring-urged to engage a projection when the knob is at zero, and a cam fixed to the body of the device and arranged to disengage said element from the ring when the projection has been pushed round by the element through a predetermined angle and to maintain that disengagement on further rotation, the ring and body having external markings to indicate the circumferential advances of the ring, wherein the application of a dose and the consequent reversion of the knob to its zero position brings said element back to engage another projection while the ring remains static.

Conveniently, the ring will be between the knob and the body of the device.

In the preferred form there will be ratchet teeth internal of the ring which form the projections, and the element that engages them may then be a peg that extends in the axial direction beyond the ring for co-operation also with the cam. This may be another co-axial ring, but with its circular aperture expanded outwards over a sector corresponding to the pitch between adjacent teeth. The radius of most of this aperture will be less than that of the circle tangential to the tips of the teeth and will keep the peg engaged with it clear of them, but the expanded portion will allow the peg to move outwards so that it can engage a tooth registering with that portion.

The cam ring will be positioned so that initially, at the zero position of the knob, the peg lies at one circumferential end of the enlargement and, when the knob is rotated, it will move towards the other end, there to be forced radially inwards to clear the teeth on further rotation of the knob.

The peg may be at the free end of a generally spiral finger whose other end rotates with the knob, the finger being of a plastics material and being so shaped and dimensioned that it acts as a spring.

Another preferred embodiment of the present invention is of the form having a non-rotatable plunger retractable from the rear end of a syringe housing to set a dose and movable forwards into the housing on ejection of the dose, the counter comprising a unidirectionally rotatable sleeve with multi-start internal screw threading carried by the housing, a projection resiliently carried by the plunger, which passes through the sleeve and which, through its projection and the screw threading, generates rotation of the sleeve as it is retracted, the minimum dose requiring the projection to traverse at least the full axial length of the sleeve and the screw threading being shaped so that the resilient projection jumps threads on forward movement of the plunger, with the sleeve being held against counter-rotation, and external markings on the sleeve and housing to indicate the circumferential advances of the sleeve.

The unidirectional rotation can be achieved by having a ratchet engagement between the sleeve and the housing.

The screw threading will conveniently be coarse pitch square section grooves and the length of the sleeve will be such that the rear end of each part-helical groove will register in the axial direction with the forward end of the adjacent groove. However, to ease the jumping of the threads, the sides of the grooves that face circumferentially and slightly rearwardly can be chamfered at their rear ends so that, as the plunger moves forward, the projection hits a sloping surface that wedges the projection inwards onto the land area between adjacent grooves. It then snaps out into the adjacent groove and emerges from the forward end of that groove, leaving the sleeve rotated from its pre-dose setting position by an amount equal to the circumferential spacing of the grooves.

When the next dose is set, the projection re-enters the groove previously vacated and indexes the sleeve around again by the same amount.

Figure 2:
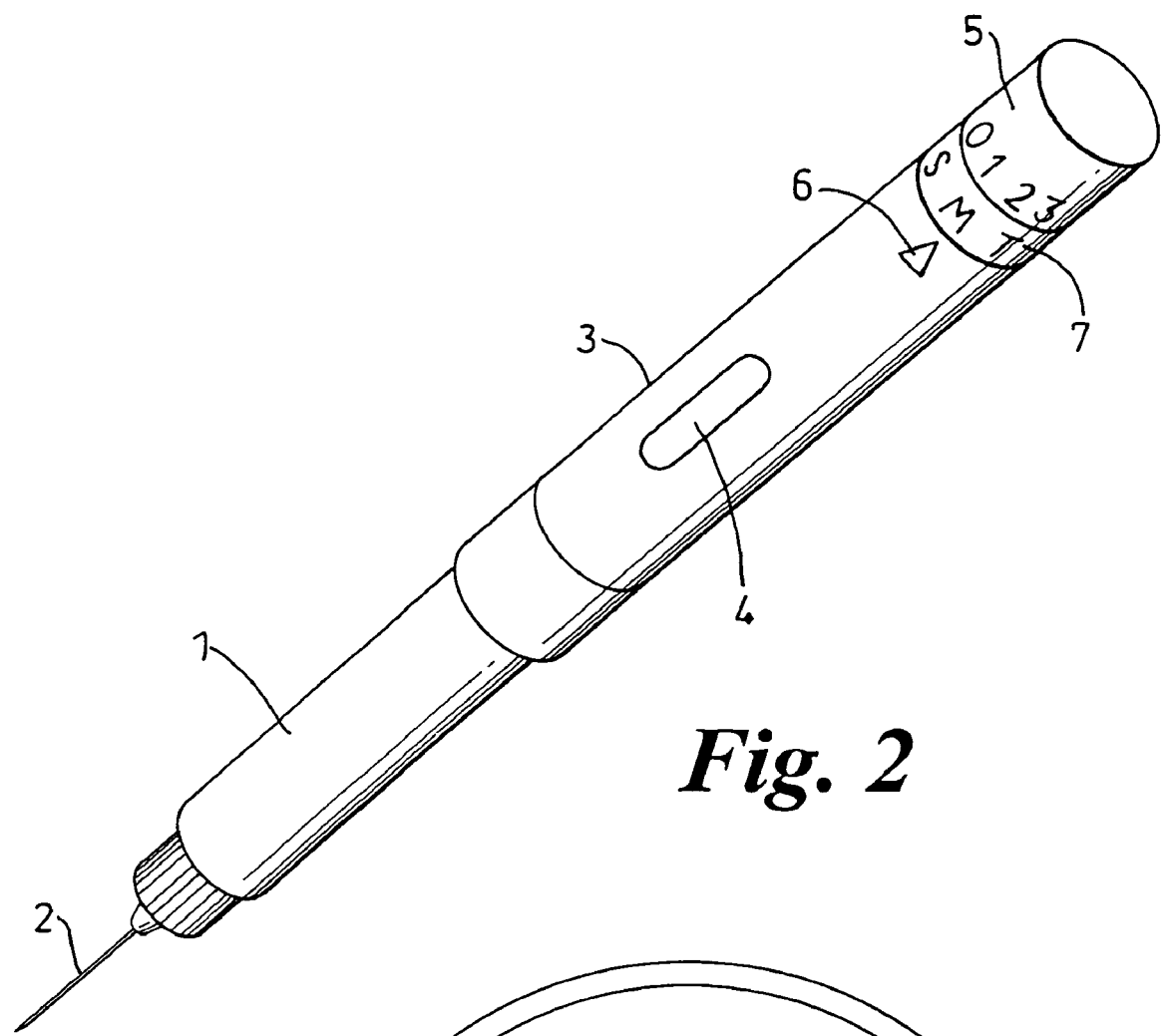
Figure 3:
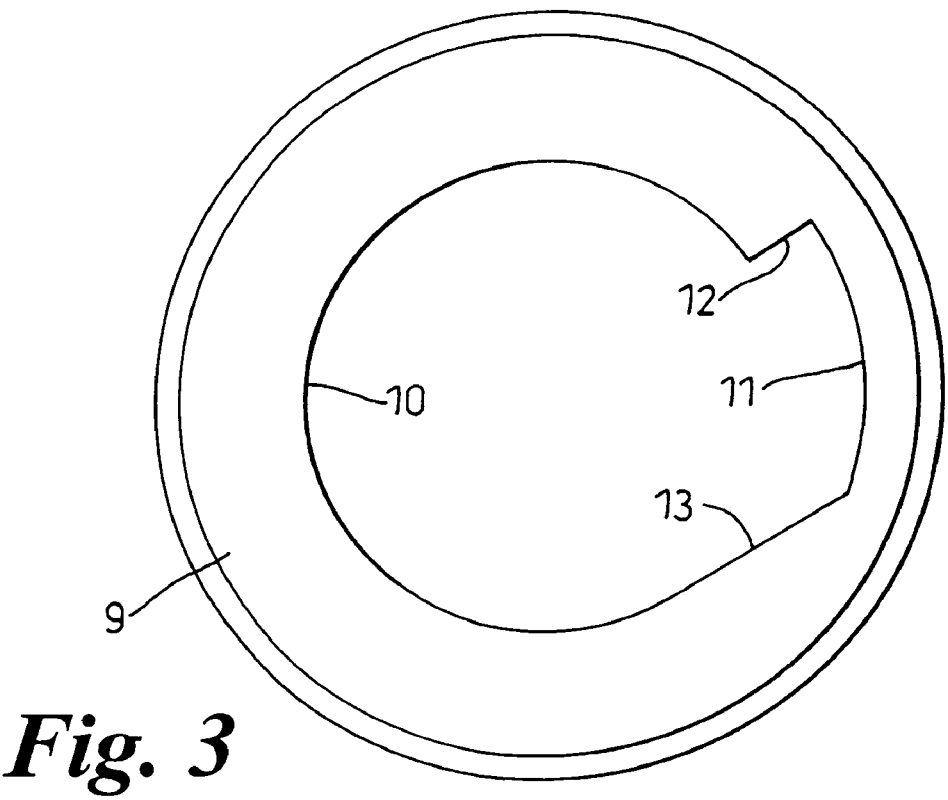
Figure 4A:
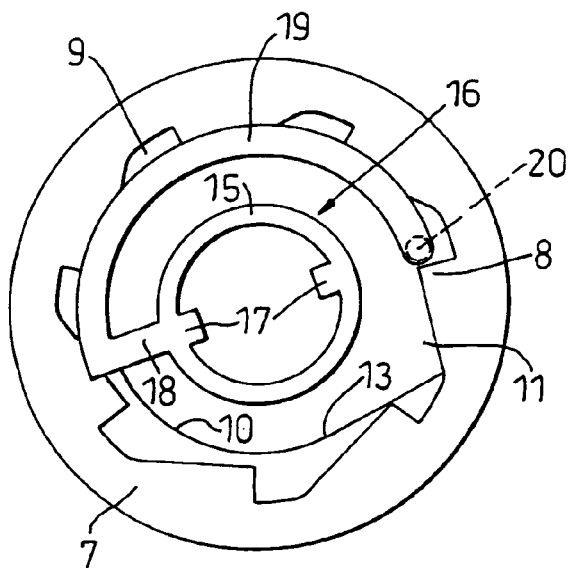
Figure 4B:
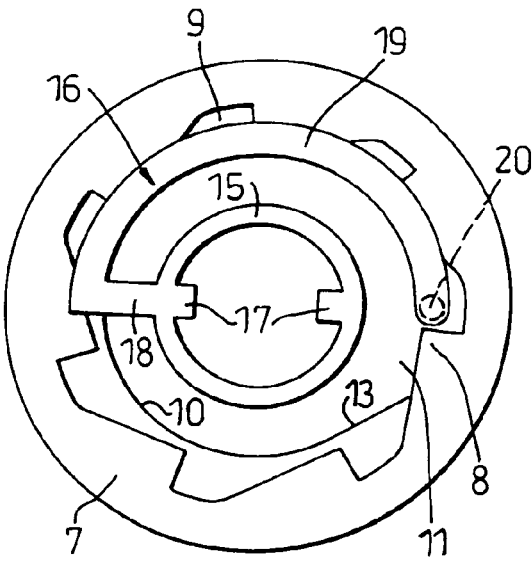
Figure 4C:
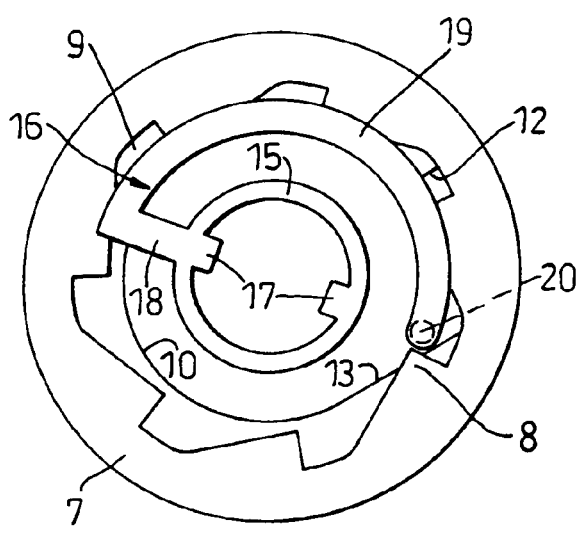
Figure 4D:
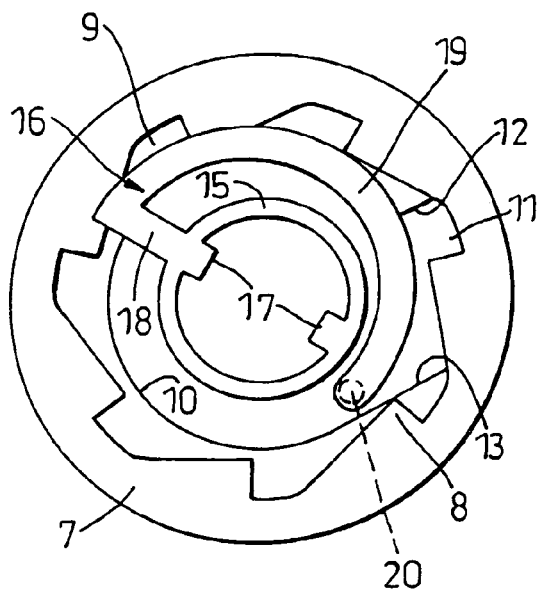
Figures 5A, 5B, 6:
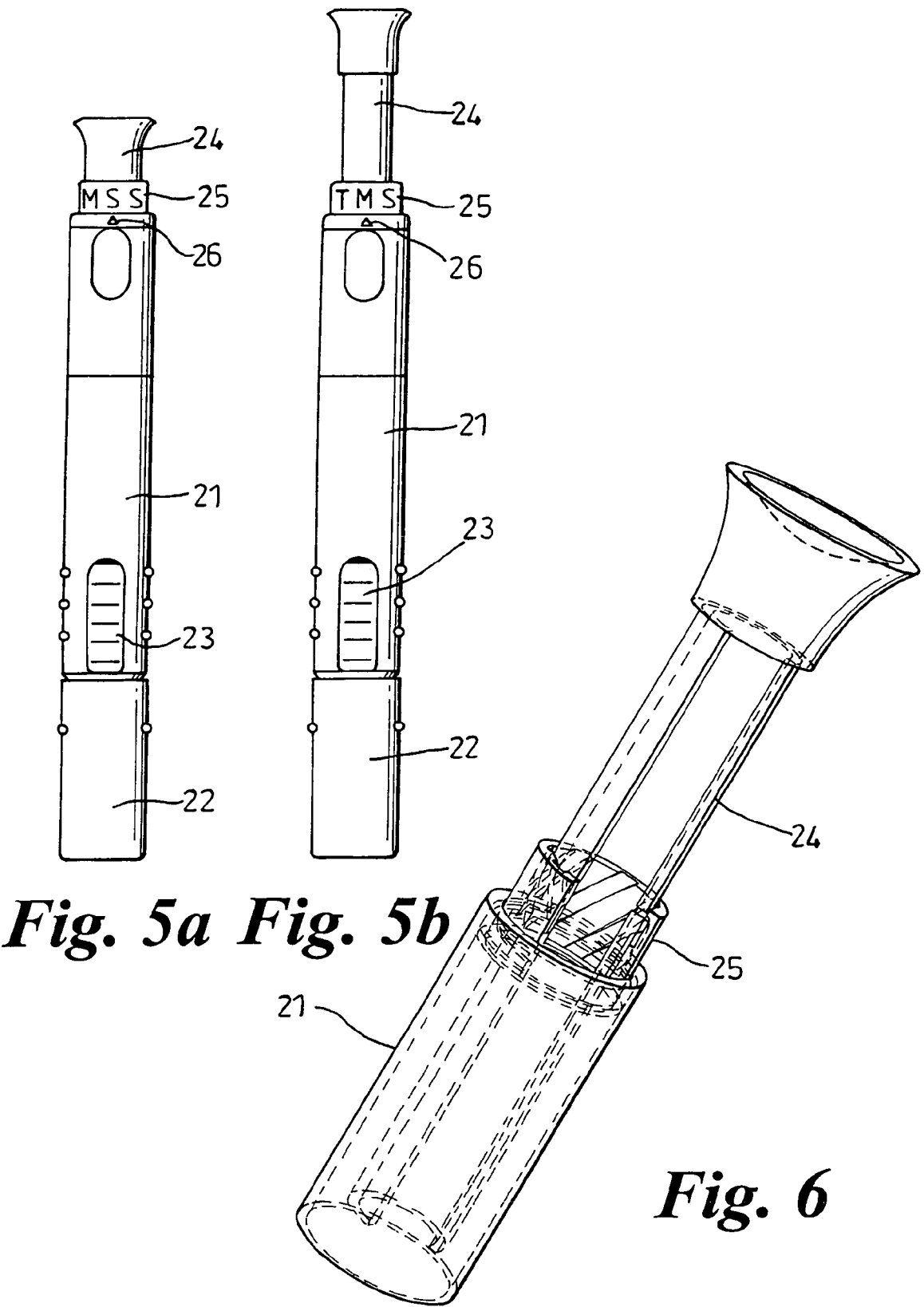
Figure 7:
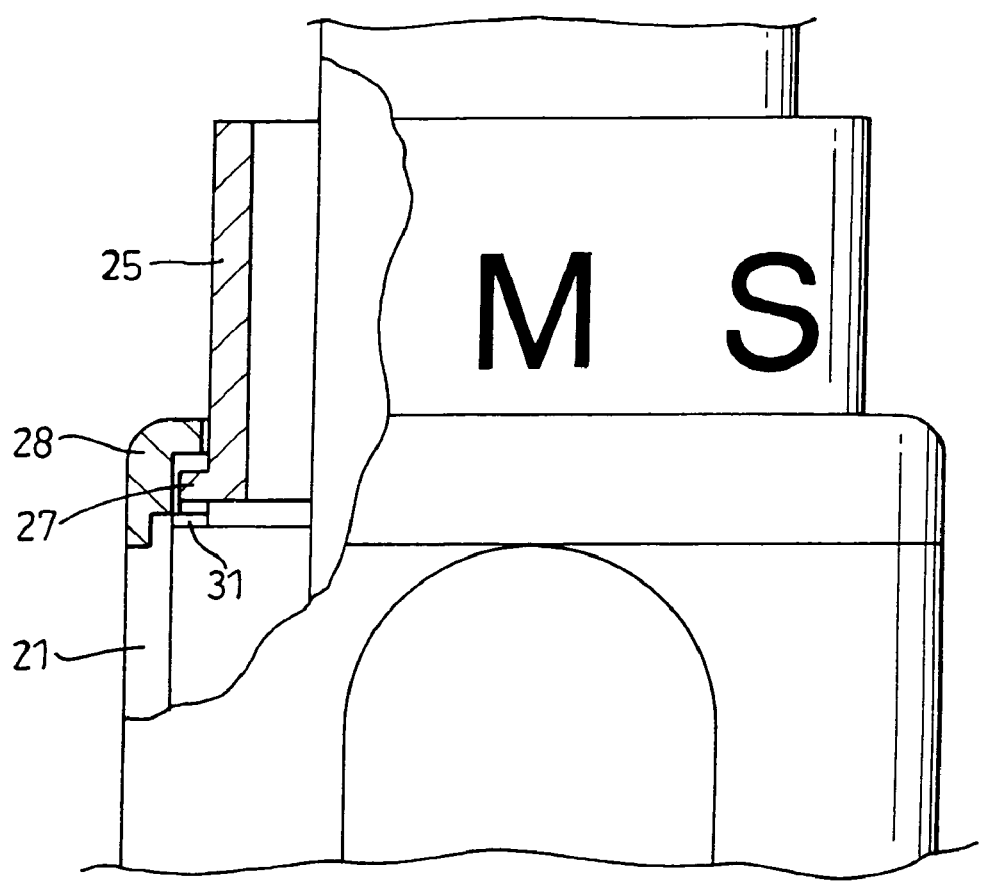
Figure 8:
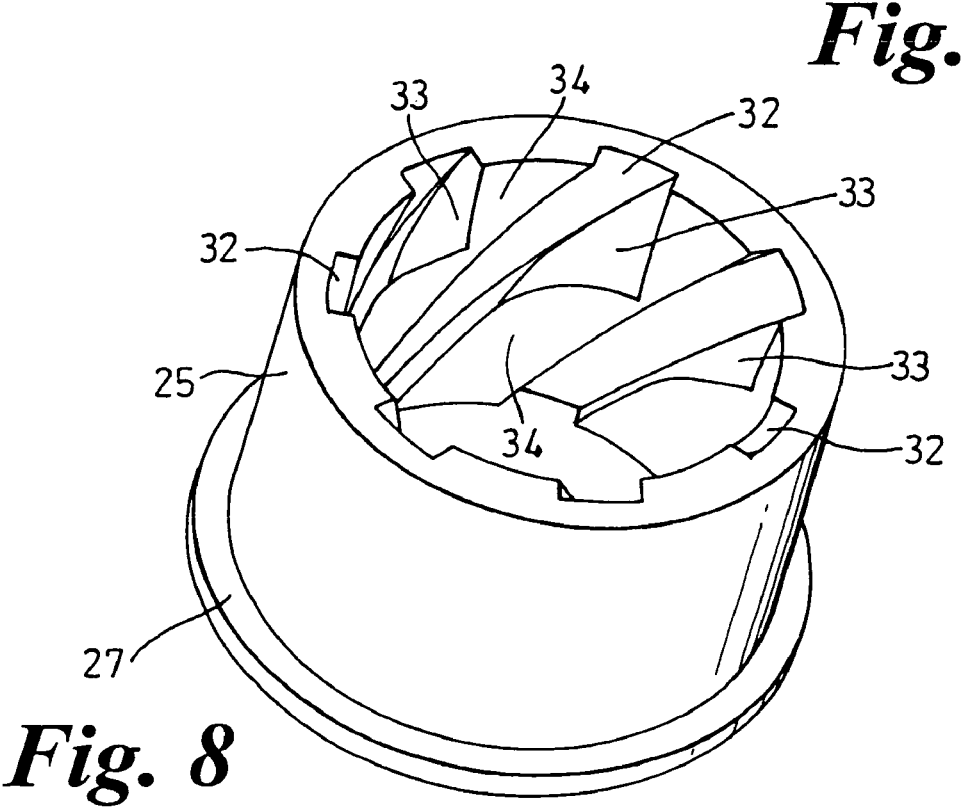
Figure 9:
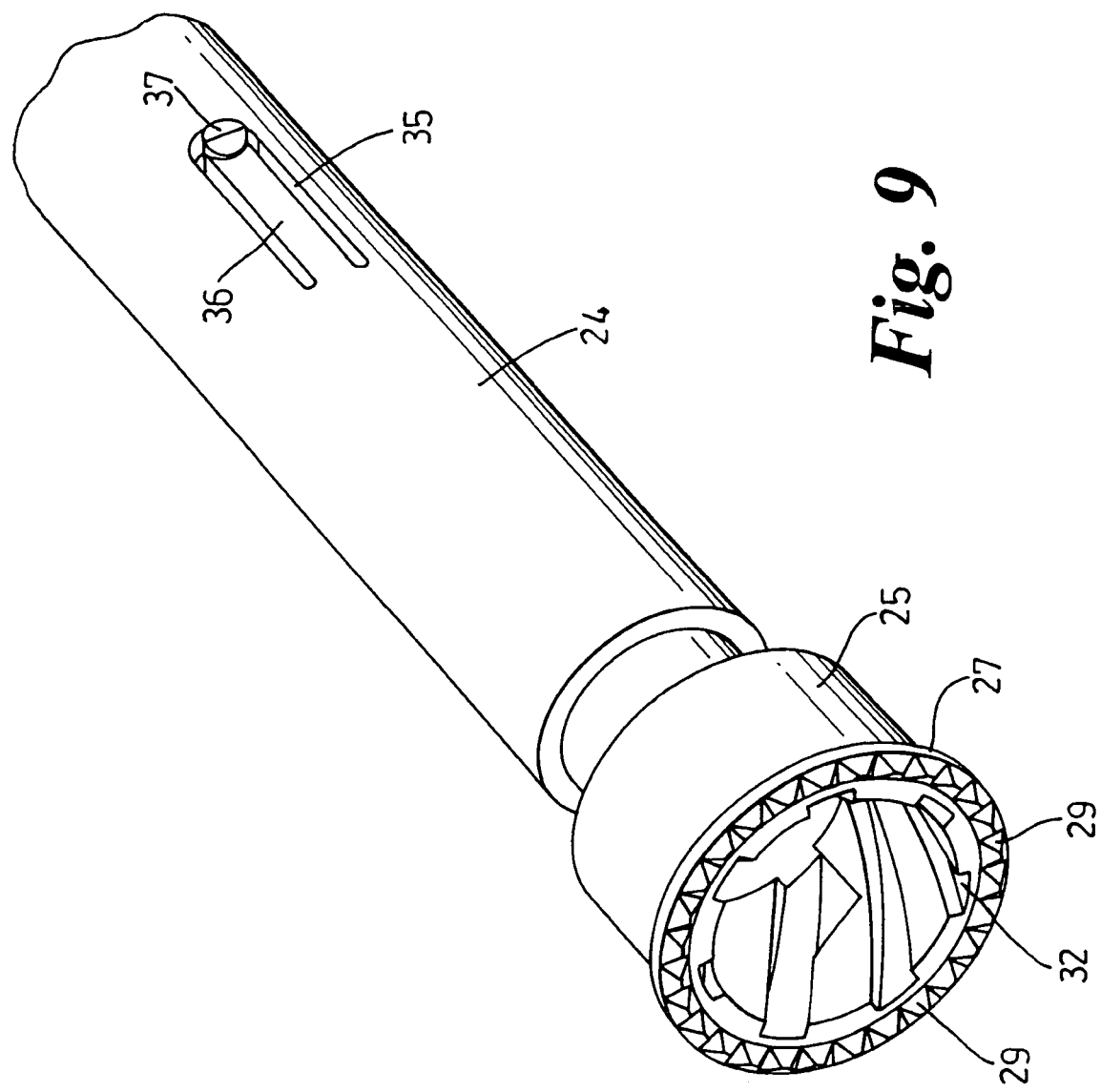
Figure 10:
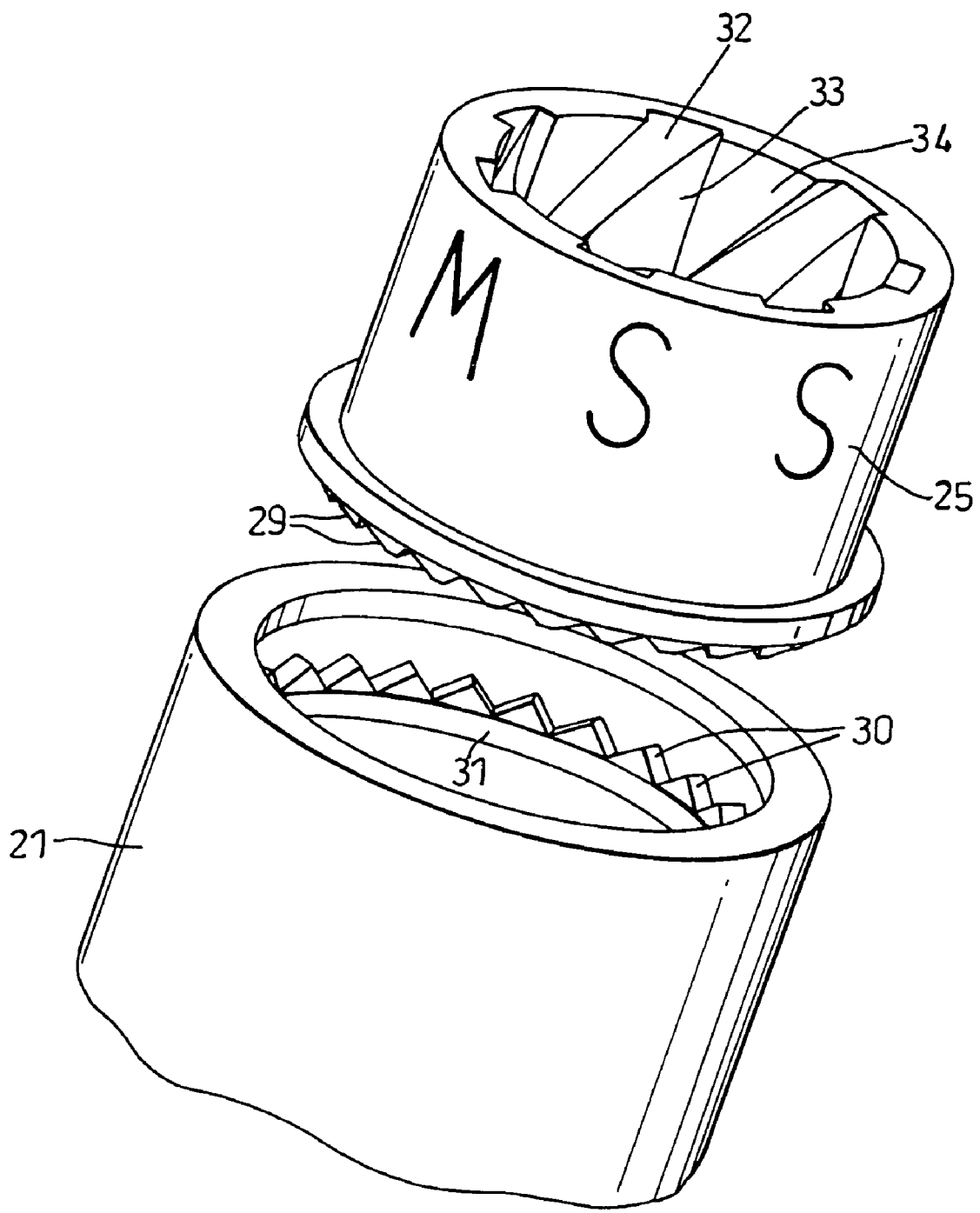

For a better understanding of the invention, embodiments thereof will now be described, by way of example, with reference to the accompanying drawings, in which:

FIG. 1 is a perspective exploded view of the rear end of an injection device with a dose counter, FIG. 2 is a perspective view of the device as assembled, FIG. 3 is a plan view of a cam ring forming part of the dose counter, FIG. 4 shows a sequence of plan views of the dose counter as the injection device is operated, FIG. 5 shows side views of another injection device before and after dose setting, FIG. 6 is a perspective view, in ghost, of the device of FIG. 5, FIG. 7 is an enlarged detail, in partial axial section, of the device showing a dose counter, FIG. 8 is a perspective view from the rear of a sleeve forming a major part of the dose counter, FIG. 9 is a perspective view from the front of the sleeve, with part of a plunger by which a dose is set, and FIG. 10 is an exploded perspective view of the sleeve and the rear end of the housing of the injection device.

The injection device of FIGS. 1 to 4 is mostly of conventional form with a cylindrical housing 1 to receive the cartridge of a syringe whose needle 2 projects from the forward end. An actuating mechanism for the syringe plunger is housed in a barrel 3 which attaches to the rear end of the housing 1. A trigger 4 releases this mechanism to eject the dose, which is set by a rotatable knob 5 at the rear end of the barrel 3. A circumferential scale on the knob 5 has numbers to register with a marker 6 on the barrel 3, and the knob is clicked round from the zero position until the desired number is opposite the marker 6. When the trigger 4 is pressed the corresponding dose is ejected and the knob 5 returns to the zero position.

However, between the knob 5 and the barrel 3 there is a co-axial ring 7 whose outer cylindrical surface, flush with those of the barrel and knob, is marked with letters indicating the days of the week. These are regularly spaced around the ring, and internally that ring has a corresponding number of ratchet teeth 8. The rear end of the barrel 3 is plugged by another co-axial ring 9, this having a mostly circular aperture with a part-cylindrical surface 10, but with an enlargement 11. One circumferential end 12 of this enlargement is radial to the ring 9 and the other end is tangential to the surface 10 and forms a cam 13. The end 12 faces in the opposite circumferential direction to the radial working faces of the ratchet teeth 8, the radius of the surface 10 is less than that of the circle tangential to the tips of those teeth and the radius of the enlargement 11 is equal to that of the circle through the roots of the teeth.

The knob 5 has a co-axial shaft 14 extending through these rings 7 and 9 into the barrel 3 to co-operate with mechanism for setting the dose. The shaft 14 is axially grooved and closely fitted by a hub 15 of an indexer 16, the hub having internal splines 17 which engage the grooves in the shaft so that the indexer rotates with the knob 5. The exterior of the hub has a short radial projection 18 at the outer end of which there is integrally formed a semi-circular finger 19 co-axial with the hub 15 in its relaxed state. Being of moulded plastics, it will have a certain resilience and be able to act as a spring. Although not a true spiral, it approximates to that shape. At the end of the finger 19 there is a peg 20 extending parallel to the axis and of greater length than the thickness of the ring 7.

When assembled, as in FIG. 4a, the indexer 16 lies immediately to the rear of the ring 7 with the finger 19 bearing on the sides of several teeth 8, and with the peg 20 engaged with the working face of one such tooth and extending forward into the enlargement 11, where its tip is adjacent the end 12. One of the letters on the outer surface of the ring 7 is in registry with the marker 6.

When the injection device is to be used, the knob 5 is rotated from its zero position, and this rotates the indexer 16, which through its peg 20 turns the ring 7 by pushing on one of the teeth 8. This movement is shown in FIGS. 4b and 4c. But when the latter position is reached, the free end portion of the peg 20 meets the cam 13, and on continued rotation of the knob 5, the peg 20 is forced radially inwards to clear the tooth 8 that it has just been pushing against. This is shown in FIG. 4d. The ring 7, having been shifted through one-seventh of a complete revolution is then left stationary while the knob 5 is turned further to whatever dose is required. There is thus a last-motion connection between knob 5 and ring 7.

When the trigger 4 is pressed, the knob 5 winds back again to its zero position, taking with it the indexer 16. The peg 20 is still held clear of the ring 7 until it hits the sloping side of the tooth following the one which it had previously pushed. As the knob finally reverts to zero, the peg 20 slides along that slope and then snaps outwardly after passing the tip.

Although when the finger 19 is bent into tighter curvature during dose setting it reduces its engagement with the sides of certain teeth, it will be seen from FIG. 4d that there is still enough to maintain its axial location.

There will now show on the exterior of the injector a new letter opposite the marker 6 indicating to the user that the day's dose has been administered.

It will be understood that rings 7 and 9 of different geometry and different markings could be fitted to cater for a pattern of injections different from one a day for a week.

There are other types of injection devices where, instead of setting the dose by rotating a knob, a plunger is simply pulled back to a selected degree from the rear end of the housing for the syringe. A counter for this type of device is shown in FIGS. 5 to 10.

The device has a barrel 21 with a forward end cap 22 that initially protects the needle of a syringe 23 within the barrel. At the rear end of the barrel there is a plunger 24 which can be pulled back from the FIG. 5a to the FIG. 5b position, thereby setting the dose to be administered. During this retraction, as will be described in more detail below, a sleeve 25 co-axially carried at the rear end of the barrel 21, and through which the plunger 24 passes, is indexed round in steps indicated by an arrow 26 on the barrel co-operating with letters on the outside of the sleeve 25 corresponding to days of the week. In this example, the sleeve is moved from Sunday to Monday by the dose setting. When the plunger moves forwards and the dose is ejected the sleeve remains static.

Referring to FIGS. 7 to 10, the sleeve 25 has an outward flange 27 at its forward end by which it is made captive to the barrel 21 through a cap 28. The forward side of this flange 27 has an annular array of teeth 29 which co-operate with a complementary set of teeth 30 on an inwardly projecting rib 31 of the barrel 21. This limits the forward movement of the sleeve 25, but there is enough axial play allowed by the cap 28 for the teeth 29 to ride over the teeth 30. Although illustrated as symmetrical, the teeth will preferably be shaped as for ratchets so that, when engaged, rotation in one direction only is possible.

Internally the sleeve 25 is formed with part-helical grooves 32, square cut and open at both ends. They are evenly spaced, and there are seven of them. The rear end of each groove 32 is aligned in the axial direction with the forward end of the adjacent groove. Towards the rear end of each groove the side that faces circumferentially and slightly rearwardly is chamfered so that there is a sloping ramp 33 leading inwards and forwards onto the part-cylindrical land area 34 between adjacent grooves 32.

The plunger 24 is tubular, and at an intermediate point it has a U-shaped cut out 35 which forms a tongue 36 pointing forwardly, and at the free end of this tongue there is an outward projection or stud 37. The thickness and nature of the plastics material of which the plunger is made renders the tongue 36 stiffly resilient.

In the position of FIG. 5a, the stud 37 is forward of the sleeve 25, but aligned with the forward end of one of the grooves 32. As the plunger 24 is retracted, the stud enters that groove and, acting on the side facing circumferentially and forwardly urges the sleeve 25 round by screw-action. The teeth 29, 30 allow this. When the stud 37 emerges from the rear end of the groove, the sleeve has been indexed round one seventh of a complete revolution. This movement corresponds to setting the minimum dose; larger doses may be set, with the stud 37 drawing well clear to the rear of the sleeve 25, but whatever dose is set the sleeve only rotates by that predetermined amount.

When the dose is administered, the plunger is moved forwards and the stud 37 re-enters the groove 32 by which it indexed the sleeve. But this time it meets the chamfer 33, and the tongue 36 is flexed inwards by a wedging action between the stud 37 and that chamfer. The stud 37 then reaches the land area 34, and subsequently snaps out into the next groove, at its forward end. This thread jumping action pushes the ratchet teeth 29, 30 together, although this may be achieved with more certainty by spring action, and the sleeve 25 is prevented from rotating back. When the dose has been administered, the plunger 24 is in the FIG. 5a position again, but with a new letter showing against the arrow, indicating that the dose for that day has been taken.

The invention claimed is:

1. A dose application counter for use with an injection device with a dose setting element which in use is moved from an initial position to set a dose, comprising a counter member connected by a lost motion connection to the dose setting element, wherein movement of said dose setting element in use by and beyond an amount to set an effective dose causes an incremental movement of said counter member to register indication of a usage of the injection device, and return of said dose setting element to said initial position is not effective to move said counter member.

2. A dose application counter according to claim 1 for an injection device of the form having a dose setting knob rotatable with respect to the body of the device, the counter comprising a rotatable ring with an annular array of projections co-axial with the knob, the minimum dose requiring the knob to be turned from a zero position through an angle at least as great as the angular spacing of adjacent projections, an element rotatable with the knob and spring-urged to engage a projection when the knob is at zero, and a cam fixed to the body of the device and arranged to disengage said element from the ring when the projection has been pushed round by the element through a predetermined angle and to maintain that disengagement on further rotation, the ring and body having external markings to indicate the circumferential advances of the ring, wherein the application of a dose and the consequent reversion of the knob to its zero position brings said element back to engage another projection while the ring remains static.

3. A dose counter as claimed in claim 2, wherein the ring is positioned between the knob and the body of the device.

4. A dose counter as claimed in claim 3, wherein the projections are formed by ratchet teeth internal of the ring, and the element that engages the teeth is a peg that extends in the axial direction beyond the ring for co-operation also with the cam.

5. A dose counter as claimed in claim 4, wherein the peg is at the free end of a generally spiral finger whose other end is rotationally fast with the knob, the finger being of a plastics material and being so shaped and dimensioned that it acts as a spring.

6. A dose counter as claimed in claim 2, wherein the projections are formed by ratchet teeth internal of the ring, and the element that engages the teeth is a peg that extends in the axial direction beyond the ring for co-operation also with the cam.

7. A dose counter as claimed in claim 6, wherein the peg is at the free end of a generally spiral finger whose other end is rotationally fast with the knob, the finger being of a plastics material and being so shaped and dimensioned that it acts as a spring.

8. A dose counter as claimed in claim 2, wherein the cam is in the form of another co-axial ring, but with its circular aperture expanded outwards over a sector corresponding to the pitch between adjacent teeth, the radius of most of the aperture being less than that of the circle tangential to the tips of the teeth.

9. A dose application counter according to claim 1, for an injection device of the form having a non-rotatable plunger retractable from the rear end of a syringe housing to set a dose and movable forwards into the housing on ejection of the dose, the counter comprising a unidirectionally rotatable sleeve with multi-start internal screw threading carried by the housing, a projection resiliently carried by the plunger, which passes through the sleeve and which, through its projection and the screw threading, generates rotation of the sleeve as it is retracted, the minimum dose requiring the projection to traverse at least the full axial length of the sleeve and the screw threading being shaped so that the resilient projection jumps threads on forward movement of the plunger, with the sleeve held against counter-rotation, and external markings on the sleeve and housing to indicate the circumferential advances of the sleeve.

10. A dose counter as claimed in claim 9, wherein the unidirectional rotation is achieved by having a ratchet engagement between the sleeve and the housing.

11. A dose counter as claimed in claim 9, wherein the screw threading comprises coarse pitch square section grooves and the length of the sleeve is such that the rear end of each part-helical groove registers in the axial direction with the forward end of the adjacent groove.

12. A dose counter as claimed in claim 11, wherein the sides of the grooves that face circumferentially and slightly rearwardly are chamfered at their rear ends so that, as the plunger moves forward, the projection hits a sloping surface that wedges the projection inwards onto the land area between adjacent grooves, so that the projection will then snap into the adjacent groove.

13. A dose counter as claimed in claim 1, wherein the lost motion connection comprises:
    an indexer configured to engage internal teeth of a coaxial ring.

14. A dose counter as claimed in claim 13, wherein the indexer comprises:
    a hub with internal splines configured to engage a shaft of a knob;
    a finger bearing on sides of several of the internal teeth, the finger being attached to the hub via a radial projection; and
    a peg attached to the finger, the peg being configured to turn the coaxial ring by pushing on one of the teeth.

15. A dose application counter for use with an injection device with a dose setting element which in use is moved from an initial position by a selected amount to set a dosage volume, said dose application counter comprising:
    a counter member connected by a lost motion connection to the dose setting element, wherein movement of said dose setting element in use by and beyond an amount to set an effective dosage volume causes a preset increment of movement of said counter member that is independent of the amount of said dose setting movement, thereby to register indication of a usage of the injection device, and return of said dose setting element to said initial position is not effective to move said counter member.

16. A dose counter as claimed in claim 15, wherein the lost motion connection comprises:
    an indexer configured to engage internal teeth of a coaxial ring.

17. A dose counter as claimed in claim 16, wherein the indexer comprises:
    a hub with internal splines configured to engage a shaft of a knob;
    a finger bearing on sides of several of the internal teeth, the finger being attached to the hub via a radial projection; and
    a peg attached to the finger, the peg being configured to turn the coaxial ring by pushing on one of the teeth.

18. A dose application counter for use with an injection device with a dose setting element which in use is moved from an initial position by a user-selected amount to set a dosage volume, said dose application counter comprising:

a counter member being indexed relation to said device by preset increments to register a count of doses; and a mechanism for indexing said counter member by a preset increment in response to movement of said dose setting element in use by and beyond a magnitude to set an effective dosage volume, the preset indexing increment being independent of said magnitude of movement and the dose setting element, said mechanism including a driver surface that moves with said dose setting element and engages a drive surface on said counter member to move said counter member through said increment and to disengage on further movement.

19. A dose counter as claimed in claim 18, wherein the mechanism comprises:

an indexer configured to engage internal teeth of a coaxial ring.

20. A dose counter as claimed in claim 19, wherein the indexer comprises:

a hub with internal splines configured to engage a shaft of a knob;

a finger bearing on sides of several of the internal teeth, the finger being attached to the hub via a radial projection; and a peg attached to the finger, the peg being configured to turn the coaxial ring by pushing on one of the teeth.

* * * * *